(12) United States Patent
Pavlin

(10) Patent No.: US 6,350,889 B1
(45) Date of Patent: Feb. 26, 2002

(54) INK JET PRINTING COMPOSITIONS CONTAINING ESTER-TERMINATED DIMER ACID-BASED OLIGO (ESTER/AMIDE)

(75) Inventor: Mark S. Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 09/338,991

(22) Filed: Jun. 24, 1999

(51) Int. Cl.$^7$ ................. C07C 230/00; C07C 231/00
(52) U.S. Cl. .................. 554/58; 554/25; 554/26; 554/51; 554/57; 554/68; 554/69
(58) Field of Search ............... 554/25, 26, 51, 554/57, 58, 68, 69

(56) References Cited

U.S. PATENT DOCUMENTS

| | | | |
|---|---|---|---|
| 3,653,932 A | 4/1972 | Berry et al. | 106/22 |
| 3,715,219 A | 2/1973 | Kurz et al. | 106/22 |
| 3,769,215 A | 10/1973 | Sturwold et al. | 252/19.5 |
| 4,157,990 A | 6/1979 | Lindner et al. | 252/56 S |
| 4,341,671 A | 7/1982 | Bolze et al. | 528/324 |
| 4,390,369 A | 6/1983 | Merritt et al. | 106/31 |
| 4,400,215 A | 8/1983 | Cooke et al. | 106/22 |
| 4,484,948 A | 11/1984 | Merritt et al. | 106/31 |
| 4,659,383 A | 4/1987 | Lin et al. | 106/27 |
| 4,684,956 A | 8/1987 | Ball | 346/1.1 |
| 4,820,346 A | 4/1989 | Nowak | 106/22 |
| 4,830,671 A | 5/1989 | Frihart et al. | 106/27 |
| 4,851,045 A | 7/1989 | Taniguchi | 106/31 |
| 4,889,560 A | 12/1989 | Jaeger et al. | 106/27 |
| 5,006,170 A | 4/1991 | Schwarz et al. | 106/20 |
| 5,011,629 A | 4/1991 | Bilbo | 260/405 |
| 5,104,586 A | 4/1992 | Brand et al. | 514/785 |
| 5,122,187 A | 6/1992 | Schwarz et al. | 106/25 |

(List continued on next page.)

FOREIGN PATENT DOCUMENTS

| | | |
|---|---|---|
| DE | 4110836 A | 10/1992 |
| EP | 187 352 B1 | 7/1986 |
| EP | 206 284 A2 | 12/1986 |
| EP | 307 933 A2 | 9/1988 |
| EP | 326 647 A2 | 9/1988 |
| EP | 367 979 A | 5/1990 |
| GB | 909363 | 10/1962 |
| JP | JO 1-110527 A | 4/1989 |
| WO | WO 86/00300 | 1/1986 |
| WO | WO 94/04619 | 3/1994 |
| WO | WO 98/26013 | 6/1998 |

OTHER PUBLICATIONS

Chem. Abstr., 123:222020, 1995.*
Chem. Abstr., 122:42631, 1995.*

* cited by examiner

Primary Examiner—Deborah D. Carr
(74) Attorney, Agent, or Firm—Seed Intellectual Property Law Group PLLC

(57) ABSTRACT

A compound of formula (1), and compositions containing a plurality of such compounds, wherein, independently at each occurrence, $R^1$ is a linear alkyl group having at least twenty carbons; $R^2$ is selected from the diradical that results when two carboxyl groups are removed from polymerized fatty acid, and a linear $C_{4-12}$ hydrocarbon group, with the proviso that at least one occurrence of $R^2$ is the diradical that results when two carboxyl groups are removed from polymerized fatty acid; $R^3$ is a diradical selected from $C_{2-36}$ hydrocarbons and $C_{4-30}$ poly(alkyleneoxides); X is selected from O and NH such that $X-R^3-X$ is selected from $O-R^3-O$ and $NH-R^3-O$; and n represents a number of repeating units selected from 1–5, may be used as a vehicle for hot melt printing inks, including inks for ink jet printing.

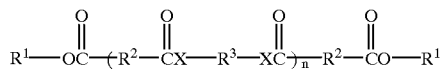

(1)

12 Claims, 1 Drawing Sheet

U.S. PATENT DOCUMENTS

| | | | | |
|---|---|---|---|---|
| 5,141,559 | A | 8/1992 | Shinozuka et al. | 106/27 |
| 5,151,120 | A | 9/1992 | You et al. | 106/27 |
| 5,194,638 | A | 3/1993 | Frihart et al. | 554/47 |
| 5,286,288 | A | 2/1994 | Tobias et al. | 106/20 B |
| 5,350,446 | A | 9/1994 | Lin et al. | 706/27 R |
| 5,354,368 | A | 10/1994 | Larson, Jr. | 106/22 A |
| 5,397,388 | A | 3/1995 | Fujioka | 106/28 A |
| 5,455,326 | A | 10/1995 | Parker | 528/335 |
| 5,496,879 | A | 3/1996 | Griebel et al. | 524/320 |
| 5,536,871 | A | 7/1996 | Santhanam | 560/196 |
| 5,597,856 | A | 1/1997 | Yu et al. | 524/227 |
| 5,645,632 | A | 7/1997 | Pavlin | 106/31.29 |
| 5,667,568 | A | 9/1997 | Sacripante et al. | 106/20 R |
| 5,759,247 | A | 6/1998 | Gregory et al. | 106/31.45 |
| 5,779,779 | A | 7/1998 | Jolly | 106/31.29 |
| 5,788,749 | A | 8/1998 | Breton et al. | 106/31.6 |
| 5,788,751 | A | 8/1998 | Sawada | 106/31.29 |
| 5,800,600 | A | 9/1998 | Lima-Marques et al. | 106/31.29 |
| 5,817,169 | A | 10/1998 | Sacripante et al. | 106/31.43 |
| 5,844,020 | A | 12/1998 | Paine et al. | 523/161 |
| 5,863,319 | A | 1/1999 | Baker et al. | 106/31.29 |
| 5,876,492 | A | 3/1999 | Malhotra et al. | 106/31.58 |
| 5,881,648 | A | 3/1999 | Pavlin | 101/491 |
| 5,902,841 | A | 5/1999 | Jaeger et al. | 523/161 |
| 5,919,839 | A | 7/1999 | Titterington et al. | 523/161 |
| 5,922,114 | A | 7/1999 | Sawada et al. | 106/31.29 |
| 5,932,630 | A | 8/1999 | Kovacs et al. | 523/161 |
| 5,936,008 | A | 8/1999 | Jones et al. | 523/161 |
| 5,938,826 | A | 8/1999 | Baker et al. | 106/31.29 |
| 5,942,368 | A | 8/1999 | Akiyama et al. | 430/176 |
| 5,952,402 | A | 9/1999 | Paine et al. | 523/161 |
| 5,954,865 | A | 9/1999 | Sawada | 106/31.29 |
| 5,965,196 | A | 10/1999 | Sawada | 427/161 |
| 5,966,150 | A | 10/1999 | Lester et al. | 347/43 |
| 5,969,003 | A | 10/1999 | Foucher et al. | 523/160 |
| 5,980,621 | A | 11/1999 | Inaishi et al. | 106/31.29 |
| 5,989,325 | A | 11/1999 | Sacripante et al. | 106/31.27 |
| 5,989,385 | A | 11/1999 | Oeltjen et al. | 156/330.9 |
| 5,994,453 | A | 11/1999 | Banning et al. | 524/590 |
| 5,997,765 | A | 12/1999 | Furuta et al. | 252/299.01 |
| 6,004,709 | A | 12/1999 | Renfer et al. | 430/58.65 |
| 6,018,005 | A | 1/2000 | Banning et al. | 525/457 |
| 6,022,909 | A | 2/2000 | Meinhardt et al. | 523/161 |
| 6,022,910 | A | 2/2000 | Nishizaki et al. | 523/161 |
| 6,028,138 | A | 2/2000 | Hahn et al. | 524/590 |
| 6,037,396 | A | 3/2000 | Sawada | 524/231 |
| 6,042,227 | A | 3/2000 | Meinhardt et al. | 347/99 |
| 6,048,925 | A | 4/2000 | Titterington et al. | 524/590 |
| 6,059,870 | A | 5/2000 | Taylor et al. | 106/31.43 |
| 6,059,871 | A | 5/2000 | Boils et al. | 106/31.57 |
| 6,093,239 | A | 7/2000 | Baker et al. | 106/31.29 |
| 6,096,125 | A | 8/2000 | Breton et al. | 106/31.43 |
| 6,099,625 | A | 8/2000 | Bradbury et al. | 106/31.27 |
| 6,099,631 | A | 8/2000 | Tregub et al. | 106/31.85 |
| 6,106,602 | A | 8/2000 | Ouchi et al. | 106/31.61 |
| 6,110,264 | A | 8/2000 | Banning et al. | 106/31.29 |
| 6,113,231 | A | 9/2000 | Burr et al. | 347/103 |
| 6,113,678 | A | 9/2000 | Malhotra | 106/31.29 |
| 6,117,223 | A | 9/2000 | Malhotra | 106/31.29 |

INK JET PRINTING COMPOSITIONS CONTAINING ESTER-TERMINATED DIMER ACID-BASED OLIGO (ESTER/AMIDE)

TECHNICAL FIELD OF THE INVENTION

The present invention relates to hot-melt inks and oligomeric components thereof having ester and optional amide groups, as well as methods for printing with such inks.

BACKGROUND OF THE INVENTION

Hot-melt inks are characterized by being solid at room temperature and molten at an elevated temperature at which the hot-melt ink is applied to a substrate. Hot-melt inks are widely used in ink jet printing, and have also been suggested for use in flexographic, intaglio and gravure printing.

Ink jet printing is a well-known process for the non-contact printing of substrates such as paper, plastic films, metal foils and the like. In essence, ink jet printing ejects a stream of liquid ink through a very small orifice, and thereafter, at a certain distance from the orifice known as the breakup distance, the stream separates into minute uniformly-sized droplets. The ink droplets travel through the air until they hit a substrate, whereupon the ink forms an image on the substrate.

Various technologies have been developed to direct jet ink in an image-wise fashion from the printhead of a printing device to a substrate. In one technology, called drop-on-demand, the printhead passes over a substrate and ejects droplets of ink only when and where ink is desirably deposited on the substrate. Drop-on-demand technology is commonly employed in desktop ink jet printers.

In contrast, in a process known as continuous stream jet printing, the printhead is constantly ejecting ink droplets as it passes over a substrate, or as the substrate passes before the printhead. A guidance system is stationed between the printhead and the substrate, so ink droplets are directed either to a specific location on the substrate or to a recirculation gutter if the droplets being ejected should not be allowed to contact the substrate. A typical continuous stream ink jet printer employs inks that can be given an electric charge, and the guidance system is an electrostatic field that will interact with and direct the charged ink droplets to a desired location. Continuous stream jet ink printing is more commonly seen in industrial printing than in desk top printing.

Jet inks suitable for either drop-on-demand or continuous stream ink jet printing can be classified either as liquid jet inks or hot-melt jet inks. Either type of ink typically contains both colorant and carrier, where the carrier is a material that dissolves or suspends the colorant. A liquid jet ink is liquid at room temperature, and is typically at about room temperature while being stored in a printhead prior to being ejected. A simple liquid jet ink is composed of an aqueous carrier and a water-soluble dye as the colorant. After a liquid jet ink contacts a substrate, the solvent typically evaporates or wicks away from the colorant, leaving the colorant visible at the site where the ink initially contacted the substrate.

In contrast, a hot-melt jet ink is solid at room temperature, and is heated to a molten state prior to being ejected from an ink jet printhead. Upon contacting the substrate, which is typically at room temperature, the molten hot-melt ink will cool and solidify. A simple hot-melt ink is composed of wax as the carrier and a pigment or dye as the colorant. All, or nearly all, of the components of a hot-melt ink remain at the site where the molten ink contacts the substrate, i.e., there is little or no wicking or evaporation of a hot-melt ink.

An ink composition useful in jet ink printing should have certain properties. It is highly desirable that the ink display a consistent breakup length, droplet viscosity, and at least in continuous stream jet printing, a constant droplet charge under the conditions employed during the jet ink printing process. To meet these requirements, the jet ink composition must have stable viscosity, stable resistance properties, and should not dry out upon aging.

A major problem with liquid jet inks arises because they contain substantial amounts of water and/or organic solvent, which evaporate upon standing so that these inks dry out and cake. This can cause blocking of the printhead orifice(s). A further problem is that loss of volatile solvents causes the inks to increase in viscosity, which will cause substantial changes in the performance of the inks. Also, a porous substrate such as paper tends to cockle and/or distort when printed with high quantities of liquid jet ink. In addition, organic solvents in a liquid jet ink can evaporate after contacting the substrate, and this may cause health problems for some persons nearby.

Another problem associated with the presence of liquid solvents in a liquid jet ink is that these solvents cause the colorant to bleed into the printed substrate, which is typically porous, with the consequence that the printing displays poor resolution. While specially coated porous substrates may overcome this problem, such special substrates are expensive and not generally necessary for other types of printing, e.g., reprographic printing, which work fine with "plain paper", i.e., standard non-coated sheet. At least in an office setting, it is highly desirable that all printing, including ink jet printing, be done on "plain paper" or standard transparencies.

Hot-melt inks offer a number of advantages over liquid inks. For example, when liquid ink is used to deposit colorant on a porous substrate, the colorant tends to be carried into the substrate as the liquid carrier wicks into the substrate. This causes a reduction in print density and some loss in print resolution. In contrast, the rapid solidification of a hot-melt ink ensures that the colorant is fixed to the surface of the substrate, with a corresponding increase in print density and resolution. A further advantage is that there is little or no cockle associated with the printing of hot-melt inks, which is in distinct contrast to printing done with liquid inks. Still another advantage is that hot-melt inks are easier to transport without spillage than liquid inks.

For several reasons, the adhesion of colorant to a substrate may also be superior in hot-melt printing. For instance, because all of the carrier in a hot-melt ink stays with the colorant at the surface of the printed substrate, rather than evaporating or wicking away from the colorant as occurs in printing with liquid inks, a hot-melt carrier is more available to assist in fixing the colorant to the substrate surface. Also, carriers which are solid at room temperature will naturally have better fixing properties than liquid carriers. Looking specifically at jet ink printing, hot-melt inks offer the advantage of having essentially no volatile components. Thus, there is no evaporation of components in a hot-melt ink, and so no corresponding problems with changes in ink viscosity, caking and health risks due to solvent evaporation, as seen with liquid inks.

To a significant extent, the properties of the carrier determine the properties of a jet ink. The prior art discloses several materials that may be used as a carrier, sometimes called a vehicle, a binder or a solid organic solvent, in hot-melt jet inks. U.S. Pat. No. 3,653,932 discloses to use diesters of sebacic acid (a solid linear $C_{10}$ dicarboxylic acid)

and paraffinic alcohols having 12 or less carbons. U.S. Pat. No. 4,390,369 discloses to use natural wax. U.S. Pat. No. 4,659,383 discloses to use $C_{20-24}$ acids or alcohols. U.S. Pat. No. 4,820,346 discloses to use aromatic sulfonamides. U.S. Pat. No. 4,830,671 discloses to use short-chain polyamides. U.S. Pat. No. 5,151,120 discloses to use the ethyl ester of stearic acid (a solid linear, $C_{18}$ carboxylic acid). U.S. Pat. No. 5,354,368 discloses to use tall oil rosin. The foregoing are exemplary of the prior art directed to hot-melt ink carriers.

Despite the significant amount of research that has been done in the area of carriers for hot-melt inks, there remains a need in the art for superior carrier materials useful in hot-melt inks, and for inks having such carrier materials.

SUMMARY OF THE INVENTION

In one aspect, the invention provides a compound of formula (1):

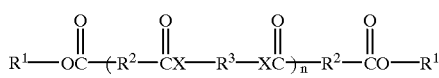
(1)

wherein, independently at each occurrence, $R^1$ is a linear alkyl group having at least twenty carbons; $R^2$ is selected from the diradical that results when two carboxyl groups are removed from polymerized fatty acid, and a linear $C_{4-12}$ hydrocarbon group, with the proviso that at least one occurrence of $R^2$ is the diradical that results when two carboxyl groups are removed from polymerized fatty acid; $R^3$ is a diradical selected from $C_{2-36}$ hydrocarbons and $C_{4-30}$ poly(alkyleneoxides); X is selected from O and NH such that X—$R^3$—X is selected from O—$R^3$—O and NH—$R^3$—O; and n represents a number of repeating units selected from 1–5.

In another aspect, the invention provides a composition including a plurality of compounds as described above.

In another aspect, the invention provides a composition that includes an image-forming agent and at least one compound as described above.

In another aspect, the invention provides a process that includes the step of reacting together various reactants to provide a reaction mixture. The reactants include polymerized fatty acid or reactive equivalent thereof, monoalcohol or reactive equivalent thereof, and at least one difunctional reactant selected from aminoalcohol or reactive equivalent thereof and diol or reactive equivalent thereof. The reactants are reacted together to provide a reaction mixture having an acid number of less than 25. In a related aspect, the invention provides compounds and compositions prepared by this process.

In another aspect, the invention provides a method of printing. The method includes the step of contacting a substrate with an ink. The ink includes an image-forming component and a compound as described above.

These and related aspects of the invention are described further below.

DETAILED DESCRIPTION OF THE INVENTION

Figure 1:
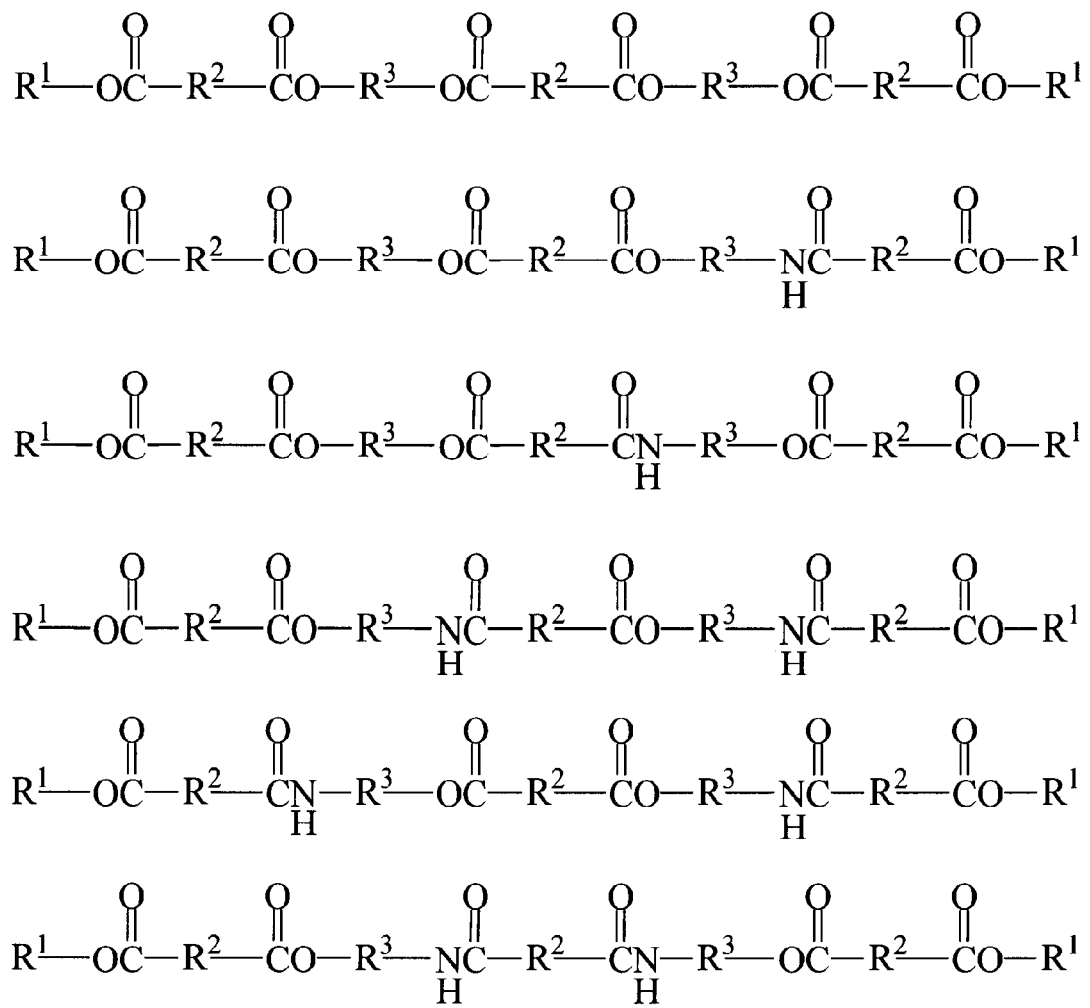
FIG. 1 provides chemical structures for certain compounds of the present invention.

As briefly summarized above, the present invention provides compounds and compositions, useful as ink components, methods of making the compounds, compositions and inks, and methods of printing.

In one aspect, the invention provides a compound of formula (1),

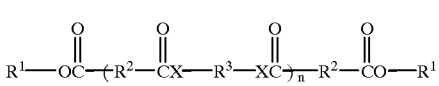
(1)

wherein, independently at each occurrence, $R^1$ is a linear alkyl group having at least twenty carbons; $R^2$ is selected from the diradical that results when two carboxyl groups are removed from polymerized fatty acid, and a linear $C_{4-12}$ hydrocarbon group, with the proviso that at least one occurrence of $R^2$ is the diradical that results when two carboxyl groups are removed from polymerized fatty acid; $R^3$ is a diradical selected from $C_{2-36}$ hydrocarbons and $C_{4-30}$ poly(alkyleneoxides); X is selected from O and NH such that X—$R^3$—X is selected from O—$R^3$—O and NH—$R^3$—O; and n represents a number of repeating units selected from 1–5.

The compounds defined by formula (1) have various characterizing features. These features include the structure

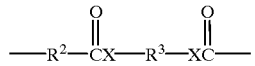

where this structure will occur either one, two, three, four, or five times in a compound of formula (1), depending on the selection of "n". Because this structure may repeat itself in a compound of formula (1), it will be referred to herein as the repeating unit. Within the repeating unit, X represents either oxygen (O) or nitrogen substituted with hydrogen (NH). Thus, a compound of formula (1) has at least four carbonyl (C=O) groups adjacent to either O or NH.

A compound of formula (1) is basically linear, and has an ester group near each terminus. Between these two terminal ester groups, are either two (when n=1), four (when n=2), six (when n=3), eight (when n=4) or ten (when n=5) internal carbonyl groups selected from ester and amide groups. The present invention provides compounds of formula (1) wherein all of the carbonyl groups are ester groups, i.e., all of the internal carbonyl groups are adjacent to an oxygen. The present invention also provides compounds of formula (1) wherein the internal carbonyl groups are both ester and amide. However, for every amide group there is at least one internal ester group, and whenever an $R^3$ in formula (1) is bonded to an amide group, then that $R^3$ is also bonded to an ester group. Accordingly, the repeating unit within the parentheses of formula (1) contains either two ester groups (when X—$R^3$—X is O—$R^3$—O) or has one ester and one amide group (when X—$R^3$—X is NH—$R^3$—O). As used herein "NH—$R^3$—O" is synonymous with "O—$R^3$—NH", and to illustrate this point, six structure encompassed by formula (1) when n=2 are shown in FIG. 1.

Because compounds of formula (1) may contain more than one repeating unit, the compounds may be referred to as oligomeric, and a specific compound may be referred to as an oligomer. A compound will contain at least three ester groups, and may contain one or more amide groups. Accordingly, for convenience, the compounds may be referred to herein as oligo(ester/amide)s.

In compounds of formula (1), $R^1$ is selected from linear alkyl groups, and particularly linear alkyl groups having at least 20 carbons. As used herein, linear alkyl groups are saturated hydrocarbon groups that are formed from a chain of methylene (—$CH_2$—) groups. In other words, the alkyl group will consist of a chain of repeating —$CH_2$— groups terminated, on one end, by the oxygen to which $R^1$ is shown bonded in formula (1), and on the other end by a hydrogen atom.

The $R^1$ groups have at least 20 carbon atoms in order that the oligo(ester/amide) of formula (1), and compositions containing such oligo(ester/amide)s, will have a sufficiently high softening point to be commercially useful in ink jet printing. In general, and up to a certain point, as the number of carbon atoms in an $R^1$ group increases, a compound of formula (1) will tend to have a higher softening point. When an oligo(ester/amide) contains $R^1$ groups having less than 20 carbon atoms, the compound will typically have a softening point below about 50° C., perhaps below 25° C. if the number of carbon atoms in $R^1$ is made sufficiently small. The oligo(ester/amide) of the invention preferably has a softening point above about 50° C., in order that it is not tacky, and is easily handled without loosing its shape. When the softening point of a compound (or a composition containing a compound) falls below about 50° C., the compound or composition may melt and/or become tacky when exposed to elevated temperatures as may be experienced during storage or transport.

In one aspect, the $R^1$ groups each have more than 20 carbon atoms. In another aspect, the $R^1$ groups each have at least 22 carbons, and in other aspects, at least one of the $R^1$ groups in an oligo(ester/amide) of formula (1) has 24, 26, 28, 30, 32, 34, 36, 38, 40, 42, 44, 46, 48, 50 or more carbons. In one aspect, the $R^1$ groups each have 30–50 carbon atoms.

The oligo(ester/amide)s of formula (1) contain two $R^1$ groups, one at each end (termini) of the compound. The identity of $R^1$ at one occurrence is independent of the identity of $R^1$ at the other occurrence. For example, the $R^1$ groups in formula (1) may be a $C_{20}$ alkyl group at one end of the compound, and a $C_{21}$ alkyl group at the other end. In one aspect of the invention, the two $R^1$ groups in formula (1) are identical, or at least contain numbers of carbon atoms within a common specified range. For example, $R^1$ may include $C_{30-50}$ hydrocarbons. In this embodiment, the compounds contain $R^1$ groups that are formed from at least 30, but less than 50, carbon atoms.

In formula (1), at least some of the $R^2$ groups will have a structure resulting from the polymerization of unsaturated fatty acid. The polymerization of unsaturated fatty acids is a well known, and long-established process, particularly in the naval stores industry. To produce polymerized fatty acid, unsaturated monomeric fatty acid is heated, typically in the presence of an acidic clay catalyst, to cause the monomeric fatty acid molecules to covalently bond together. This polymerization reaction results in the formation of fatty acid dimers (dimer acid), trimers (trimer acid), and higher order species. Polymerized fatty acid is typically a mixture of structures, where individual dimer, trimer, etc. acids may be saturated, unsaturated, cyclic, acyclic, etc. Thus, a detailed characterization of the structure of polymerized fatty acid is not readily available. However, good discussions of fatty acid polymerization may be found in, e.g., U.S. Pat. No. 3,157,681 and *Naval Stores—Production, Chemistry and Utilization,* D. F. Zinkel and J. Russel (eds.), Pulp. Chem. Assoc. Inc., 1989, Chapter 23.

In formula (1), $R^2$ represents the diradical that results when polymerized fatty acid has two carboxyl groups removed. In a preferred practice, the compounds of the invention are prepared from polymerized fatty acid, and two of the carboxyl groups thereof undergo condensation reactions in the formation of the inventive compounds. These two reactive carboxyl groups thus remain attached to the $R^2$ groups, as shown in formula (1), where $R^2$ is flanked by two carbonyl groups (where the two carbonyl groups derive from the two carboxyl groups in the polymerized fatty acid). Accordingly, while $R^2$ in the oligo(ester/amide) of formula (1) is described in terms of a structure that would be present if two carboxyl group were removed, in fact, in the formation of the oligo(ester/amide) according to a preferred method, $R^2$ remains attached to the two carboxyl groups.

While at least some of the $R^2$ groups in formula (1) will have the diradical structure resulting when two carboxyl groups are removed from polymerized fatty acid, some of the $R^2$ groups may be linear chains of 4 to 12 carbon atoms, i.e., may be linear $C_{4-12}$ hydrocarbon groups. Thus, some of the $R^2$ groups may have the structure —$(CH_2)_{4-12}$— resulting from a chain of 4 to 12 methylene groups.

The addition of some linear $C_{4-12}$ hydrocarbon groups in oligo(ester/amides) of formula (1) typically increases the melting point of the compounds, and compositions containing same. However, the compounds and compositions of the invention preferably have melting points of less than 120° C. Accordingly, if linear $C_{4-12}$ hydrocarbon groups are included as the $R^2$ portion of formula (1), such groups preferably constitute a minor number of such groups, i.e., less than 50% of the $R^2$ groups are linear $C_{4-12}$ hydrocarbon groups. In various aspects of the invention, less than 40%, 30%, 20%, 10%, and 5% of the $R^2$ groups are linear $C_{4-12}$ hydrocarbon groups. In one aspect, all of the $R^2$ groups are the diradical that results when polymerized fatty acid has two carboxyl groups removed.

In formula (1), $R^3$ is a diradical selected from $C_{2-36}$ hydrocarbons and $C_{4-30}$ poly(alkyleneoxides). The $C_{2-36}$ hydrocarbon contains at least two, and no more than 36 carbon atoms, in addition to hydrogen atoms. The carbon atoms may be arranged in a linear, branched or cyclic fashion, and may be joined by any combination of single, double and triple bonds, so long as a stable structure results. In various embodiments, $R^3$ is a saturated hydrocarbon diradical, is a linear hydrocarbon diradical, and/or contains 2–30, 2–20, 2–10, 2–6, 2–4, or 2 carbon atoms.

$R^3$ may also be a $C_{4-30}$ poly(alkyleneoxide). As used herein, the term "poly(alkyleneoxide)" has its standard meaning in the art, and refers to a plurality (i.e., at least two) alkylene groups joined together by ether groups (i.e., oxygen atoms). The poly(alkyleneoxide) diradicals of the present invention have at least four carbon atoms, and thus include the poly(alkyleneoxide) of the structure —$CH_2CH_2$—O—$CH_2CH_2$—. More generally, the poly(alkyleneoxide) has the structure (—$R^4$—O—)$_m$ wherein $R^4$ is an alkylene group (i.e., one or a chain of methylene groups) and m is an integer such that the poly(alkyleneoxide) group has at least 4, but less than about 30, carbon atoms. Generally, $R^4$ is independently selected at each occurrence, however, in one aspect, $R^4$ is the same at each occurrence in an $R^3$ group. In various aspects, the poly(alkyleneoxide) group has 4–28, 4–20, 4–16, 4–10, or 4 carbon atoms.

In formula (1), and at each occurrence, $R^3$ is independently selected from the above-described groups. In two aspects of the invention, all of the $R^3$ groups are either $C_{2-36}$ hydrocarbon or $C_{4-30}$ poly(alkyleneoxide). In general, incorporation of a poly(alkyleneoxide) group into a compound of formula (1) will cause the compound, and compositions containing the compound, to have a lower melting point, and a lower melt viscosity. The invention also provides compositions that include a plurality of compounds of formula (1).

As used herein, the term plurality means "at least two" where the "at least two" compounds have non-identical structures. Typically, when a compound of formula (1) is prepared by a preferred method as described in detail below, the compound will be formed in admixture with one or more other compounds of formula (1). This admixture is a composition of the present invention. In one preferred composition, all compounds will have the same $R^1$, $R^2$ and $R^3$ groups, however, they will have different values for "n". Thus, the composition may contain a mixture of compounds having 4, 6, 8, 10 and 12 carbonyl groups.

While a composition of the invention will contain at least two of these compounds, it may contain additional compounds as well, including compounds of formula (1) wherein n is zero and/or n is an integer greater than 5. Compositions of the invention typically include a mixture of oligo(ester/amide)s of formula (1) in addition to, for example, by-products that are formed during the compound-forming reaction. While the oligo(ester/amide)s of formula (1) may be purified from by-products and/or one another using, e.g., chromatography or distillation, the by-products are typically either minimal in amount or impart desirable properties to a composition containing the inventive compounds, and thus need not be separated from the oligo(ester/amide)s of formula (1) in order for a suitable ink jet resin to be formed. For convenience, the word "composition" will be used below to refer to the material that is useful in an ink jet ink, although it must be recognized that a single purified compound of formula (1) might also be useful in the ink, so long as it has the properties desired in the compositions described below.

In one composition of the invention, compounds of formula (1) wherein n is 1–5 constitute at least 50 mol %, preferably at least 75 mol %, more preferably at least 90 mol %, and still more preferably at least 95 mol %, based on all of the compounds of formula (1) in the composition regardless of the value for n, i.e., allowing n to assume any value. In general, as the composition contains a greater proportion of compounds of formula (1) having n greater than 5, the composition demonstrates a higher viscosity than is typically suitable for ink jet printing. In another composition of the invention, compounds of formula (1) wherein n is 1–5 constitute at least 50 wt %, preferably at least 75 wt %, more preferably at least 90 wt %, and still more preferably at least 95 mol % of those compounds of formula (1) present in the composition wherein n may assume any integer.

The average molecular weight of a composition containing a plurality of compounds of formula (1) is a reflection of the number of repeating units in an "average" compound formula (1) present in the composition. In one embodiment, the total of the compounds of formula (1) in an inventive composition have a peak molecular weight, as measured by gel permeation chromatography using polystyrene standards, of less than 8,000, or less than 5,000, or less than 3,000, or less than 2,000. In these compositions, the weight average molecular weight of the total of the oligo(ester/amide) compounds is typically less than 10,000, and in various embodiments, is less than 8,000, less than 6,000, or less than 4,000.

In another embodiment, the invention provides compositions including a plurality of compounds of formula (1), the composition having a peak molecular weight, as measured by gel permeation chromatography using polystyrene standards, of less than 8,000, or less than 5,000, or less than 3,000, or less than 2,000. According to this embodiment, the weight average molecular weight of the composition is less than 10,000, or less than 8,000, or less than 6,000, or less than 4,000.

The compositions of the invention preferably have softening point, melt viscosity, and VOC (volatile organic content) properties rendering the composition suitable for use as a component of ink jet printing inks. In formula (1), "n" represents a number of repeating units, and is an integer selected from 1, 2, 3, 4 and 5, i.e., is 1–5. In general, as the number of repeating units increases, the melt viscosity of the composition will increase and the melting point will decrease.

In order to be useful in a hot-melt ink, a composition of the invention should typically be a solid at room temperature and have a melting point below the operating temperature of the printing equipment which is used to apply the molten ink (prepared from compound(s) of formula (1)) to a substrate. When the inventive composition is used in jet ink printing with conventional printing equipment, the composition typically has a melting point of from about 40° C. to about 150° C., preferably about 60° C. to about 140° C., and more preferably about 80° C. to about 130° C. The melting point can be measured by, e.g., the dropping point device sold by Mettler-Toledo International, Inc. (CH-8606 Greifensee, Switzerland; http://www.mt.com) as their Model FP83HT Dropping Point Cell. The melting point of the composition may be varied upon variation of the identities of $R^1$, $R^2$, $R^3$ and n in formula (1) as explained herein.

When molten, the inventive composition preferably has a viscosity, commonly termed a "melt viscosity", which is suitable for a component of a hot-melt ink. Again, the melt viscosity of the inventive composition can be varied by proper selection of the identities of $R^1$, $R^2$ and $R^3$. For incorporation into a jet ink being applied by conventional equipment, the composition should typically have a melt viscosity of less than about 300 centipoise (cP) at 150° C., and preferably has a melt viscosity of less than about 100 cP at 130° C. Melt viscosity can be conveniently measured using the Model RVTD Digital Viscometer from Brookfield Engineering Laboratories (Middleboro, Mass.; http://www.brookfieldengineering.com).

Hot-melt inks are preferably non-tacky at room temperature or even slightly elevated temperatures as might be experienced when printed materials are transported in hot weather by truck or rail. Thus, the oligo(ester/amide) is preferably non-tacky under the same conditions. Non-tacky oligo(ester/amide)s can be prepared according to the invention disclosed herein. Another preferred feature of the oligo(ester/amide) is that it is colorless. However, black hot-melt inks are commercially desirable, so colored oligo(ester/amide)s, e.g., amber or hazy compounds, and compositions containing a plurality of compounds, are also useful. Furthermore, preferred oligo(ester/amide)s are hard and are not oily.

In preparing compounds of formula (1), and compositions containing a plurality of these compounds, preferred starting materials are monoalcohol, dimer acid, and at least one difunctional reactant selected from diol and aminoalcohol, or reactive equivalents of any of these.

The monoalcohol has formula $R^1$—OH, where $R^1$ has at least 20 carbon atoms, as defined above. Exemplary monoalcohols useful in the invention include 1-eicosanol ($C_{20}$), 1-docosanol ($C_{22}$, also known as behenyl alcohol), dotriacontanol ($C_{32}$), tetratriacontanol ($C_{34}$), pentatriacontanol ($C_{35}$), tetracontanol ($C_{40}$), tetraacontanol ($C_{44}$), dopentaacontanol ($C_{54}$), tetrahexaacontanol ($C_{64}$), dohexaacontanol ($C_{72}$), etc. Essentially pure monohydric linear alcohols having greater than 20 carbon atoms are available from many sources, including Aldrich (Milwaukee, Wis.; http://www.aldrich.sial.com) and M. Michel and Company, Inc.

(New York, N.Y.). A suitable pure monohydric alcohol is behenyl alcohol, commercially available as CACHALOT™ from M. Michel and Company, Inc. (New York, N.Y.).

Alternatively, the monoalcohol may be a mixture of monohydric alcohols. Preferably, at least about 90% of the monohydric alcohols in a mixture of monohydric alcohols has at least about 20 carbon atoms, and more preferably has at least about 24 carbon atoms. The residual 10% impurity in a mixture of monohydric alcohols may have less than 20 carbon atoms, as long as the blend of monohydric alcohols has a hydroxyl value of at least about 60, preferably about 70 to about 130.

Vapor pressure osmometry (VPO), among many other techniques, may be used to characterize the number average molecular weight of a blend of alcohols. The mixtures of monohydric alcohols useful in the invention have number average molecular weights by VPO of about 200 to about 800, preferably about 300 to about 600. Pure $C_{22}$ monohydric linear alcohol has a molecular weight of 326 by VPO. Suitable mixtures of alcohols are commercially available from, e.g., Petrolite Corporation (Tulsa, Okla.) or Aston Chemicals (Bucks, United Kingdom; http://www.astonchemicals.com) under the UNILIN™ or PERFORMACOL™ trademarks. In particular the UNILIN™ (or PERFORMACOL™) product numbers 350, 425 and 550, having carbon numbers of 30–50, are preferred.

At least some of the $R^2$ groups are derived from polymerized fatty acid. Fatty acid polymerization is practiced by many businesses in the United States, and accordingly polymerized fatty acid is readily available. Quite often, the crude polymerization mixture is subjected to a purification procedure (typically, distillation) in order to provide a product that is enriched in dimer acid. In one embodiment, $R^2$ is at least 80 wt % dimeric species and less than 20 wt % non-dimeric (e.g., trimeric) species. In another embodiment, $R^2$ is at least 90 wt % dimeric species. In a still another embodiment, $R^2$ is at least 95 wt % dimeric species. Suitable polymerized fatty acids are available commercially as, for example, UNIDYME™ dimer acid from Union Camp Corporation (Wayne, N.J.), EMPOL™ dimer acid from Henkel Corporation, Emery Oleochemicals Division (Cincinnati, Ohio); PRIPOL™ dimer acid from Unichema North America (Chicago, Ill.), and SYLVADYM™ dimer acid from Arizona Chemical, division of International Paper, (Panama City, Fla.).

The $R^2$ group may be incorporated into a compound of the invention by employing "co-diacid" as one of the reactants. The co-diacid has formula HOOC—$R^2$—COOH (where $R^2$ is defined above). Co-diacids suitable for use in the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid). Such co-diacids are available from, e.g., Aldrich Chemical.

Another exemplary co-diacid for use in the present invention is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division (Charleston Heights, S.C.; http://www.westvaco.com), as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic diacids. The aromatic diacid may contain aliphatic carbons bonded to the aromatic ring(s), as in HOOC—$CH_2$—Ar—$CH_2$—COOH and the like. The aromatic diacid may contain two aromatic rings, which may be joined together through one or more carbon bonds, (e.g., biphenyl with carboxylic acid substitution) or which may be fused (e.g., naphthalene with carboxylic acid substitution). Suitable aromatic diacids are available from, e.g., Aldrich Chemical.

The $R^3$ group is conveniently introduced into oligo(ester/amide)s of formula (1) through an aminoalcohol of formula $H_2N$—$R^3$—OH or a diol of formula HO—$R^3$—OH. Such aminoalcohol reactants are also known as alkanolamines. Such diol reactants are also known as dihydric compounds or dihydric alcohols. In both the aminoalcohol and the diol, the $R^3$ group is a diradical selected from $C_{2-36}$ hydrocarbons and $C_{4-30}$ poly(alkyleneoxides), as described above. The use of aminoalcohol provides X—$R^3$—X groups equal to NH—$R^3$—O, while the use of diol provides X—$R^3$—X groups equal to O—$R^3$—O. The inventive compounds may be prepared using only diol, or only aminoalcohol, or a mixture of diol and aminoalcohol, as the difunctional reactant.

Exemplary aminoalcohols are 3-amino-propanol and 2-(2-aminoethoxy)ethanol. The hydroxyl group of the aminoalcohol is preferably a primary alcohol, and the amino group is likewise a primary amino group. Suitable aminoalcohols are available from many commercial suppliers, including the following manufacturers and/or distributors: Aldrich (Milwaukee, Wis.; http://www.aldrich.sial.com); EM Industries, Inc. (Hawthorne, N.Y.; http://www.emscience.com); Lancaster Synthesis, Inc. (Windham, N.H.; http://www.lancaster.co.uk); and Spectrum Quality Product, Inc. (New Brunswick, N.J.; http://www.spectrumchemical.com).

Representative aminoalcohols may contain an $R^3$ group which is a $C_{4-30}$ poly(alkyleneoxide), where such $R^3$ groups include, without limitation, polyethylene oxide, polypropylene oxide and copolymers (either random, alternating or block) of ethylene oxide and propylene oxide. Such oxygenated $R^3$ groups are readily introduced into a compound of formula (1) through use of JEFFAMINE™ alkanolamines (Huntsman Chemical Inc., Houston, Tex.; http://www.huntsman.com). These materials are available in a wide range of molecular weights. While some of the $R^3$ groups may contain oxygen (at least about 1%), preferably a minor number (less than 50%) of the $R^3$ groups contain oxygen, and more preferably less than about 20% of the $R^3$ groups contain oxygen.

Exemplary diols are ethylene glycol, propylene glycol, neopentyl glycol, diethylene glycol, triethylene glycol, 1,4-butanediol, 1,6-hexanediol, 1,4-cyclohexanedimethanol, and the like, all which have primary hydroxyl groups. Diols suitable as a reactant in the present invention are available from, for example, Aldrich Chemical Co. (Milwaukee, Wis.).

Reactive equivalents of diacids, monoalcohol and/or aminoalcohols or diols may be used in the invention. For example, diesters may be substituted for some or all of the diacid, where "diesters" refer to the esterification product of diacid with hydroxyl-containing molecules. However, such diesters are preferably prepared from relatively volatile hydroxyl-containing molecules, in order that the hydroxyl-containing molecule may be easily removed from the reaction vessel subsequent to monoalcohol and/or aminoalcohol/diol (both as defined herein) reacting with the diester. A lower alkyl diester, e.g., the esterification or diesterification product of diacid as defined herein and a $C_{1-4}$ monohydric alcohol (e.g., methanol, ethanol, propanol and butanol), may be used in place of some or all of the diacid in the oligo(ester/amide) forming reaction of the invention. The acid halide of the diacid may likewise be employed in place of some or all of the diacid, however such a material is typically much more expensive and difficult to handle compared to the diacid, and thus the diacid is preferred. Likewise, a hydroxyl group in the monoalcohol aminoalcohol or diol may be esterified with a volatile acid, e.g., acetic acid, prior to being employed in the oligo(ester/amide) forming reaction of the invention. While such reactive equivalents may be employed in the reaction, their presence is not preferred because such equivalents introduce undesired reactive groups into the reaction vessel.

As described herein, diacid (including dimer acid and co-diacid), monoalcohol and difunctional reactant(s) selected from aminoalcohol and diol are preferred starting materials to form the compounds and compositions of the invention. These starting materials are preferably reacted together with a stoichiometry, and under reaction conditions, such that the acid number of the resulting reaction product is less than 25, preferably less than 15, and more preferably less than 10, while the amine number is preferably less than 10, more preferably less than 5, and still more preferably less than 1. The progress of the reaction may be monitored by periodically pulling samples and measuring the acid number of the samples. Techniques to measure an acid number are well known in the art. See, e.g., ASTM D-465 (1982). Typically, a 4–8 hour reaction time at about 200–220° C. can provide an oligo(ester/amide) having an acid number of less than about 25.

To prepare an oligo(ester/amide) of the invention, the diacid, monoalcohol and difunctional reactant (diol, partially or completely replaced with aminoalcohol) are reacted together. As used herein, "reacted together" means to combine the reactants to form a reaction mixture, and maintain this mixture at an elevated temperature to achieve ester and, if desired, amide formation. Any order of combination is suitable, and heating rate is not particularly important. The final heating temperature is suitably about 150° C. to about 250° C. At temperatures below about 150° C., the rate of product formation is undesirably slow, while temperatures above about 250° C. can cause some reactant and/or product degradation, resulting in dark colored product.

Upon heating, water vapor will be evolved as the esterification and amidification reactions occurs. Preferably, the water vapor is condensed and removed from the reaction mixture as soon as it forms, thus driving the reaction to completion. A Dean-Stark trap is suitably used for this purpose. A gentle flow of an inert gas, nitrogen for example, may be passed through the reaction flask in order to facilitate removal of the water vapor. Alternatively, the water vapor is removed by application of a modest vacuum of about 20–200 mtorr.

A catalyst may be used to speed up the esterification and amidification reactions, where suitable catalysts are well known in the art and include sulfuric acid, phosphoric acid and other inorganic acids, metal hydroxides and alkoxides such as tin oxide and titanium isopropoxide, and divalent metal salts such as tin or zinc salts. When a catalyst is present, it should be used in small amounts, e.g., less than about 5 weight percent of the total mass of the reaction mixture, preferably less than about 2% and more preferably less than about 1% of the total mass of the reaction mixture. Excessive amounts of catalyst increase the cost of preparing the oligo(ester/amide), as well as often leave behind residue that may be harmful to the environment in which hot-melt ink is placed, e.g., a printhead.

Thus, the present invention provides a composition prepared by a process that includes the step of reacting together various reactants to provide a reaction mixture, where those reactants include dimer acid or reactive equivalent thereof, monoalcohol or reactive equivalent thereof, and at least one difunctional reactant selected from aminoalcohol or reactive equivalent thereof and diol and reactive equivalent thereof. The relative amounts of the reactants, and the duration of the reaction period, should be such that the resulting composition has an acid number of less than 25. The monoalcohol or reactive equivalent thereof may include monoalcohol of formula $R^1$—OH wherein $R^1$ is $C_{20+}$ linear hydrocarbon. The product composition should have a relatively low molecular weight, typically a weight average molecular weight of less than 10,000 as measured by gel permeation chromatography using polystyrene standards. In order to be used in printing, the composition should be placed in admixture with an image-forming component.

It is important to control the stoichiometry of the reactants in order to prepare oligo(ester/amide) according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dicarboxylic acid (e.g., dimer acid or sebacic acid) has two equivalents of carboxylic acid, while a mole of monoalcohol has one equivalent of hydroxyl. Furthermore, it is emphasized that the diacid has primarily only two reactive groups (both carboxylic acids, in the event the polymerized fatty acid contains some trimer acid, the polymerized fatty acid will contain some species with three reactive groups), the monoalcohol has only one reactive group (a hydroxyl group) and the aminoalcohol and diol each have only two reactive groups (one hydroxyl group and one primary amine group for the aminoalcohol; two hydroxyl groups for the diol), and these are preferably, although not necessarily, the only reactive materials present in the reaction mixture.

The following discussion will describe the preferred reaction conditions for a reaction mixture that includes diacid, monoalcohol and aminoalcohol. In analogy, the same parameters may be applied with diol replacing some or all of the aminoalcohol.

According to the invention, is it preferred that the equivalents of carboxylic acid are substantially equal to the combined equivalents of hydroxyl (contributed by monoalcohol and aminoalcohol) and amine (contributed by aminoalcohol). In other words, if the reaction mixture used to form an oligo(ester/amide) compound has "x" equivalents of carboxylic acid, "y" equivalents of amine and "z" equivalents of hydroxyl, then $0.9 < \{x/(y+z)\} \leq 1.1$, and preferably $\{x/(y+z)\}$ is substantially 1.0. Under these conditions, substantially all of the carboxylic acid groups will react with substantially all of the hydroxyl and amine groups, so that the final product contains very little unreacted carboxylic acid, hydroxyl or amine groups. In other words, each of the acid and amine numbers of a composition containing a plurality of compounds of the invention is preferably less than about 25, is more preferably less than about 15, and is more preferably less than about 10, and is still more preferably less than about 5.

When co-diacid is employed to prepare an oligo(ester/amide), the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–30 equivalent percent, and more preferably contributes 0–10 equivalent percent of the acid equivalents in the reaction mixture.

In order to prepare the composition of the invention, it is important to control the equivalents of hydroxyl, amine and carboxylic acid (or reactive equivalents thereof) used in the compound-forming reaction. In one embodiment, 1.8–2.2 equivalents of hydroxyl from monoalcohol, and 0.8–1.2 equivalents of hydroxyl from aminoalcohol are reacted with 4 equivalents of acid from polymerized fatty acid, and monoalcohol, aminoalcohol and polymerized fatty acid are essentially the only compound-forming reactants. In another embodiment, 1.9–2.1 equivalents of hydroxyl from monoalcohol, and 0.9–1.1 equivalents of hydroxyl from aminoalcohol are reacted with 4 equivalents of acid from polymerized fatty acid, and monoalcohol, aminoalcohol and polymerized fatty acid are essentially the only compound-forming reactants. In another embodiment, 2 equivalents of hydroxyl from monoalcohol, and 1 equivalent of hydroxyl from aminoalcohol are reacted with 4 equivalents of acid from polymerized fatty acid, and monoalcohol, aminoalcohol and polymerized fatty acid are essentially the only compound-forming reactants As the equivalents of hydoxyl from monoalcohol are increased (all other factors staying constant), the average molecular weight (both number and weight average) of a composition containing a plurality of oligo(ester/amide) compounds will decrease, while the average molecular weight increases as the equivalents of hydroxyl from monoalcohol is decreased. The incorporation of more difunctional reactants (i.e., more aminoalcohol and polymerized fatty acid), while maintaining a constant amount of monofunctional reactant (i.e., monoalcohol) will cause the average molecular weight of the composition to increase. Accordingly, the stoichiometry of the reactants will have a significant impact on the oligo(ester/amide)-containing composition.

Contrary to the situation for most polymeric species, the end groups in admixtures of compounds of the invention have a significant impact on the properties of the admixture. The end-groups of the compounds, being linear and formed from hydrocarbon (as required by the definition of $R^1$), will impart crystallinity to the admixture, and will tend to increase the melting point thereof. According, as more end groups are present in the admixture, i.e., as the admixture's average molecular weight decreases, the melting point of the admixture will increase. Furthermore, decreasing the average molecular weight will cause the admixture to have a lower melt viscosity.

A preferred oligo(ester/amide) of the invention is at least partially transparent, and thus does not interfere with, taint or mask the appearance of the colorant or other image-forming component in the ink. Furthermore, preferred oligo(ester/amide)s are hard, are not oily, and are non-tacky.

Another aspect of the invention is a hot-melt ink composition comprising an image-forming component and an oligo(ester/amide) as described above. The image-forming component is a material that may be detected or observed by any means. A colorant is a preferred image-forming component, where colorants may be visually detected by the human eye, or by an optical character reading device. Both dyes and pigments are suitable colorants, where extensive lists of specific dyes and pigments suitable for use in the hot-melt ink of the present invention are set forth in both of U.S. Pat. Nos. 5,286,288 and 5,122,187, where the disclosures of these two patents are incorporated herein in their entireties.

Alternatively, the image-forming component may be a magnetic material that can be scanned by a suitable reader, or a fluorescent material that can be detected upon exposure to specific wavelengths of light. While in rare instances the carrier itself may serve as an image-forming component, it is more typically the case that the carrier is a transparent material that functions primarily to suspend and disperse the image-forming component at elevated temperatures, and then helps to fix the image-forming component to a substrate after printing.

The carrier typically constitutes about 0.5 to about 97 weight percent of the hot-melt ink composition, and preferably about 80–97 weight percent of the ink composition. The image-forming component typically constitutes about 0.1–3 weight percent, preferably about 0.3–2 weight percent of the hot-melt ink composition.

The hot-melt ink composition of the invention may contain ingredients in addition to colorant and poly(ester/amide). For example, when the hot-melt ink is used in continuous jet ink printing, the ink may contain an electrolyte. When containing an electrolyte, the hot-melt ink may be induced to carry a charge, and droplets of charged hot-melt ink may be directed to either a substrate for printing, or a gutter for recycling, by adjustment of an electrostatic field through which the charged ink particles must pass. A suitable electrolyte for the hot-melt ink composition of the invention is an inorganic salt, as disclosed in, e.g., U.S. Pat. No. 5,286,288. When the electrolyte is an inorganic salt, an electrolyte-solvating and dissociating compound, as also disclosed in the '288 patent, is preferably present in the hot-melt ink composition.

Other ingredients that may be present in the hot-melt ink composition of the invention include one or more of a corrosion inhibitor, biocide, plasticizer, tackifier, surfactant, dispersing agent, antioxidant, rheology modifier and UV stabilizer.

Accordingly, the present invention provides a composition that includes an image-forming agent and a compound of formula (1):

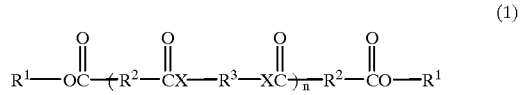

(1)

wherein, independently at each occurrence, $R^1$ is a linear alkyl group having at least twenty carbons; $R^2$ is selected from the diradical that results when two carboxyl groups are removed from polymerized fatty acid, and a linear $C_{4-12}$ hydrocarbon group, with the proviso that at least one occurrence of $R^2$ is the diradical that results when two carboxyl groups are removed from polymerized fatty acid; $R^3$ is a diradical selected from $C_{2-36}$ hydrocarbons and $C_{4-30}$ poly(alkyleneoxides); X is selected from O and NH such that X—$R^3$—X is selected from O—$R^3$—O and NH—$R^3$—O; and n represents a number of repeating units selected from 1–5. In various embodiments of the invention, the image-forming agent is a colorant, the printing composition is essentially free of any component having a boiling point of less than about 150° C. (i.e., is solventless), and/or is at a temperature in excess of 75° C.

Hot-melt ink compositions of the present invention may generally be prepared simply by combining the desired ingredients to form a mixture, and heating the mixture with stirring to form a molten homogeneous composition which is the hot-melt ink composition. A temperature in the range of about 90° C. to about 150° C. is typically adequate to achieve a homogeneous composition after a stirring time of about 5 seconds to about 10 minutes. It is also possible to melt one component of the ink, e.g., the carrier, and then add other components with stirring. When pigment is included in the hot-melt ink composition, then it may be necessary to grind the mixture of ingredients to effect a uniform dispersion of the pigment in the ink. Grinding may suitably be accomplished with a ball mill or an atritor.

As used herein, the term "hot-melt ink" denotes an ink that is a solid at room temperature and a liquid at the operating temperature of the printer employing the hot-melt ink. Typical printers for hot-melt inks heat the ink to about 110° C. to about 130° C. The hot-melt ink of the invention thus has a viscosity of about 1 centipoise (cP) to about 50 cP at a temperature of about 75° C. to about 175° C., more preferably has a viscosity of about 2 cP to about 20 cP at a temperature of about 90° C. to about 150° C., and still more preferably has a viscosity of about 5 cP to about 15 cP at a temperature of about 110° C. to about 130° C.

The hot-melt ink of the invention may be used to print on a wide variety of substrates, which may be porous or non-porous. Exemplary substrates include plastics, plastic laminates, glass, metal, paper, wood, etc. The ink may be used in drop-on-demand and continuous ink jet printers, where these printers are commercially available from many sources.

Thus, in one aspect, the invention provides a method of printing which includes the step of contacting a substrate with an ink, where the ink includes an image-forming component and a compound of formula (1),

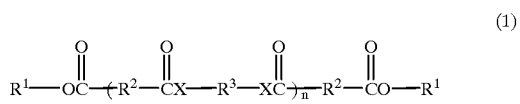

(1)

wherein, independently at each occurrence, $R^1$ is a linear alkyl group having at least twenty carbons; $R^2$ is selected from the diradical that results when two carboxyl groups are removed from polymerized fatty acid, and a linear $C_{4-12}$ hydrocarbon group, with the proviso that at least one occurrence of $R^2$ is the diradical that results when two carboxyl groups are removed from polymerized fatty acid; $R^3$ is a diradical selected from $C_{2-36}$ hydrocarbons and $C_{4-30}$ poly(alkyleneoxides); X is selected from O and NH such that $X-R^3-X$ is selected from $O-R^3-O$ and $NH-R^3-O$; and n represents a number of repeating units selected from 1–5. The contacting step may be achieved by, for example, jetting the ink from a reservoir to a substrate, where suitable substrates are paper and polyester. In one aspect, the ink has a viscosity of less than 150 cP when measured at 130° C.

The hot-melt ink may also be used in gravure and intaglio printing. To achieve such printing with a hot-melt ink, a hot-melt ink as described above is melted and the molten ink stored in a reservoir. A printing plate, which is typically warmed to a temperature of greater than or about the same as the melting point of the hot-melt ink, is then contacted with the pool of molten hot-melt ink. In this way, molten hot-melt ink is transferred to a gravure or intaglio printing plate, in essentially the same manner as liquid inks are currently transferred to a printing plate.

The printing plate, having molten hot-melt ink thereon, is then contacted with a substrate in order to transfer ink to the substrate in an image-wise fashion. The substrate, which is typically at room temperature, will immediately induce cooling of the hot-melt ink, and thereby cause the ink to become fixed to the substrate.

The following examples are set forth as a means of illustrating the present invention and are not to be construed as a limitation thereon.

EXAMPLES

In the following examples, UNILIN™ 550 alcohols were from Petrolite (Tulsa, Okla., although currently the same product is apparently available from Aston Chemicals, Aston Chemicals, Bucks, United Kingdom; http://www.aston-chemicals.com, under their PERFORMACOL™ alcohols trademark). 3-Amino-1-propanol and diglycolamine ($HO-CH_2CH_2-O-CH_2CH_2-NN_2$, also known as 2-(2-aminoethoxy)ethanol) are available from Aldrich (Milwaukee, Wis.; http://www.aldrich.sial.com. EMPOL™ dimer acid is from Henkel Corporation, Emery Oleochemicals Division (Cincinnati, Ohio; http://www.henkelcorp.com.

Example 1

A flask was charged with 90.0 g UNILIN™ 550 alcohols, 3.1 g 3-amino-1-propanol, and 58.2 g EMPOL™ 1008 dimer acid. This mixture was reacted by heating to a temperature of 220° C. over a 3 hr period to provide an intermediate product with an acid number of 27.3. This intermediate product was heated for a further 5.25 hrs. to provide oligo(ester/amide) having an acid number of 10.8.

Example 2

A flask was charged with 90.0 g UNILIN™ 550 alcohols, 4.3 g diglycolamine, and 58.2 g EMPOL™ 1008 dimer acid. This mixture was reacted by heating for 8 hours at up to 220° C., during which time some water was formed and removed by gently sweeping nitrogen gas through the flask, to provide the product oligo(ester/amide) which was a light tan color.

Example 3

A flask was charged with 156.0 g UNILIN™ 550 alcohols, 9.1 g diglycolamine, and 110.0 g EMPOL™ 1010 dimer acids. This mixture was reacted by heating to 220° C. over an 8.5 hr. period. The product oligo(ester/amide) had an acid number of 13.2 and a melt viscosity of 28.5 centipoise (cP) when measured at 130° C.

Example 4

A reaction flask fitted with a stirrer, thermocouple probe, nitrogen inlet and gas outlet was charged with 47.0 g EMPOL 1008 dimer acid, 60.0 g UNILIN 550 alcohols (50 eq. % OH), and 6.0 g cyclohexanedimethanol (50 eq. % OH, Eastman Chemical's "CHDM-D"). This mixture was heated to about 150° C. under a slow sweep of nitrogen to melt-blend the ingredients, then heated gradually, with stirring, to 225° C. over a period of 5 h. At this time, the nitrogen sweep was increased and the temperature held at 225° C. for 1 h. The product was then poured. It was a soft, tan-colored, translucent solid with Mettler dropping point of 97.3° C. and a Brookfield viscosity at 130° C. of 34.5 cP.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of formula (1):

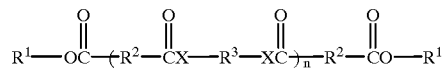
(1)

wherein, independently at each occurrence, $R^1$ is a linear alkyl group having at least twenty carbons; $R^2$ is selected from the diradical that results when two carboxyl groups are removed from polymerized fatty acid, and a linear $C_{4-12}$ hydrocarbon group, with the proviso that at least one occurrence of $R^2$ is the diradical that results when two carboxyl groups are removed from polymerized fatty acid; $R^3$ is a diradical selected from $C_{2-36}$ hydrocarbons and $C_{4-30}$ poly(alkyleneoxides); X is selected from O and NH such that X—$R^3$—X is NH—$R^3$—O; and n represents a number of repeating units selected from 1–5.

2. A compound according to claim 1, wherein independently at each occurrence, $R^1$ is a $C_{30-50}$ linear alkyl group.

3. A compound according to claim 1, wherein independently at each occurrence, $R^2$ is a diradical that results when two carboxyl groups are removed from a polymerized fatty acid.

4. A compound according to claim 1, wherein independently at each occurrence, $R^3$ is a $C_{2-20}$ hydrocarbon.

5. A composition comprising a plurality of compounds according to claim 1.

6. A composition according to claim 5 having a softening point of 50–120° C.

7. A composition according to claim 5 having a melt viscosity of less than 150 cP measured at 130° C.

8. A composition according to claim 5 having a weight average molecular weight of less than 8,000 as measured by gel permeation chromatography using polystyrene standards.

9. A composition according to claim 5 having a softening point of 50–120° C. and a melt viscosity of less than 150 cP measured at 130° C., wherein $R^1$ is a linear alkyl group having at least 22 carbons, and $R^2$ is the diradical that results when two carboxyl groups are removed from polymerized fatty acid.

10. A process comprising the step of reacting together reactants to provide a reaction product, the reactants comprising polymerized fatty acid or reactive equivalent thereof, monoalcohol of the formula $R^1$—OH wherein $R^1$ is a linear alkyl group having at least twenty carbon atoms or reactive equivalent thereof, and aminoalcohol or reactive equivalent thereof, wherein the reactants are combined under conditions of temperature and time so as to afford a reaction product, and the reaction product has an acid number of less than 25.

11. A process according to claim 10, wherein 1.8–2.2 equivalents of hydroxyl from monoalcohol, and 0.8–1.2 equivalents of hydroxyl from aminoalcohol are reacted with 4 equivalents of acid from polymerized fatty acid, and monoalcohol, aminoalcohol and polymerized fatty acid are essentially the only reactants.

12. The reaction product resulting from the process of claim 10.

* * * * *